United States Patent [19]

Binder et al.

[11] Patent Number: 4,590,203

[45] Date of Patent: May 20, 1986

[54] DERIVATIVES OF THIOPHENE-2-CARBOXYLIC ACID AND THEIR PHARMACEUTICALLY ACCEPTABLE ACID OR BASE ADDITION SALTS AND USE IN TREATMENT OF CONDITIONS CAUSED BY THROMBOXANE $A_2$

[75] Inventors: Dieter Binder; Christian Noe, both of Vienna, Austria

[73] Assignee: Laevosan-Gesellschaft m.b.H. & Co. KG, Linz, Austria

[21] Appl. No.: 548,753

[22] Filed: Nov. 4, 1983

[30] Foreign Application Priority Data

Nov. 5, 1982 [AT] Austria .................................. 4041/82

[51] Int. Cl.$^4$ .................. A61K 31/415; C07D 403/00
[52] U.S. Cl. ...................................... 514/397; 548/336
[58] Field of Search ....................... 548/336; 514/397

[56] References Cited

U.S. PATENT DOCUMENTS 4,087,536 5/1978 Budde et al. ..................... 548/336

OTHER PUBLICATIONS

Hartough, Thiophene and its Derivatives, Interscience Publishers, Inc., New York, (1952), p. 183.

Hofmann, Imidazole and its Derivatives, Part I Interscience Publishers, Inc., New York, (1953), p. 49.

Primary Examiner—Henry R. Jiles
Assistant Examiner—Robert C. Whittenbaugh
Attorney, Agent, or Firm—Sughrue, Mion, Zinn, Macpeak, and Seas

[57] ABSTRACT

The disclosure is directed to new derivatives of thiophene-2-carboxylic acid and the pharmaceutically acceptable acid or base addition salts thereof as well as to the process for the preparation thereof. The compounds of the invention have the structural formula

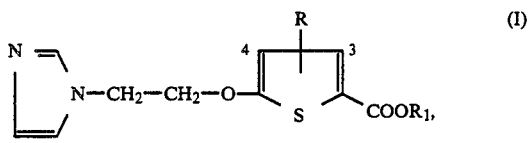

in which R in position 3 or 4 of the thiophene nucleus is hydrogen, methyl, chlorine or bromine and $R_1$ is hydrogen or $C_1$-$C_4$-alkyl. The compounds have a remarkably strong inhibitory effect on the thromboxane synthetase and are useful for the treatment of conditions such as inflammation, hypertension, thrombus, apoplexy, asthma, angina pectoris, ischemic heart diseases, ischemic conditions, migraine and vascular complications in connection with diabetes.

10 Claims, No Drawings

DERIVATIVES OF THIOPHENE-2-CARBOXYLIC ACID AND THEIR PHARMACEUTICALLY ACCEPTABLE ACID OR BASE ADDITION SALTS AND USE IN TREATMENT OF CONDITIONS CAUSED BY THROMBOXANE A₂

SUMMARY OF INVENTION

The present invention relates to novel therapeutically useful derivatives of the thiophene-2-carboxylic acid of the general formula

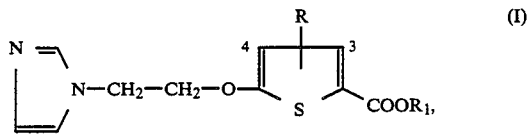

in which R in position 3 or 4 is hydrogen, methyl, chlorine or bromine and $R_1$ is hydrogen or $C_1$-$C_4$-alkyl, and the pharmaceutically acceptable acid or base addition salts thereof and to a process for the preparation of these compounds.

The novel compounds of formula (I) exhibit a strong inhibitory effect on the thromboxane synthetase without any significant inhibition of the effect of the prostacycline synthetase or cyclooxygenase enzymes from microsomes of thrombocytes, i.e. the novel compounds of formula (I) inhibit the conversion of prostaglandine-H₂ to thromboxane-B₂ via thromboxane-A₂, which is an instable intermediate and induces the irreversible aggregation of platelets and contracts smooth muscles, especially those of the blood vessels. This fact shows that the compounds of formula (I) of the invention inhibit the biosynthesis of thromboxane A₂ and are therefore suitable for the treatment of diseases caused by thromboxane A₂, such as inflammation, hypertension, thrombus, apoplexy, asthma, angina pectoris, ischemic heart diseases, ischemic conditions, migraine and vascular complications in connection with diabetes.

Of the compounds of formula (I) of the invention both the esters and the free acids have a strong effect on the thromboxane synthetase.

The process of the invention comprises the reaction of a compound of the general formula

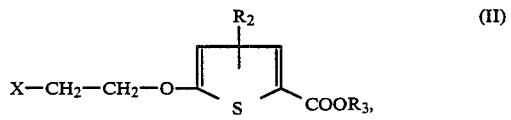

in which $R_2$ in position 3 or 4 of the thiophene nucleus is hydrogen or methyl and in position 3 is chlorine or bromine, X is a leaving group suitable for nucleophilic exchange, such as e.g. halogen, and $R_3$ is $C_1$-$C_4$-alkyl, with the alkali metal salt of imidazole of the formula

and, if desired, halogenation of the obtained compounds of formula (I), in which R is hydrogen, with a halogenating agent suitable for the electrophilic substitution, such as e.g. SO₂Hal₂ or N-Hal-succinimide, Hal being chlorine or bromine, in position 4 of the thiophene nucleus and, if desired, hydrolysis of the esters of formula (I) thus obtained, in which $R_1$ is $C_1$-$C_4$-alkyl, to give the carboxylic acids of formula (I).

DETAILED DESCRIPTION OF THE INVENTION

The reaction of the invention is carried out usually by addition of one equivalent of an alkali metal hydride, e.g. sodium hydride, to a solution of imidazole in an anhydrous inert organic solvent, such as e.g. dimethylformamide, dimethylsulfoxide, hexamethylphosphoric triamide. For the completion of formation of salts it is heated still 1 hour to 90° C., as soon as the addition of the alkali metal hydride is completed. Then the solution is cooled and the halide of formula (II) is added, preferably in equivalent amounts or in slight excess, dissolved in the same solvent.

The course of the reaction until completion may be carried out at ambient temperature, however, generally it is preferred to heat the reaction mixture, e.g. to 70° C., so as to accelerate the reaction. Under these conditions the reaction is completed usually substantially within 1 hour.

The reaction mixture is worked up in conventional manner, e.g. by removal of the solvent in vacuo, by solvent extraction and recrystallization.

Preferably sulfuryl chloride or sulfuryl bromide is used to introduce a halogen substituent in position 4 of the thiophene nucleus of the esters of formula (I), in which R is hydrogen. It is most convenient to dissolve the esters of formula (I) in a halogenated hydrocarbon, preferably chloroform, and to add sulfuryl halide diluted in chloroform or not-diluted at temperatures below −35° C. The sulfuryl halide should be used in an equivalent amount only in a slight excess. Then the reaction solution is allowed to warm up to room temperature and to react for a period up to 15 hours. The working up is carried out by adding aqueous HCl and ether, separating and neutralizing the aqueous phase, extracting the precipitating halogenated ester, most convenient with methylene chloride, removing the solvent in vacuo and purifying the product by recrystallization or column chromatography.

The acids of formula (I) may be obtained in usual way by hydrolysis catalyzed with mineralic acid or base of the corresponding esters (formula I: $R_1$=$C_1$-$C_4$-alkyl), e.g. with use of aqueous NaOH or aqueous hydrochloric acid.

The compounds of formula (I) according to the invention having a free carboxylic radical or a free amino radical may be converted in usual manner into their pharmaceutically acceptable salts. E.g. the compound of formula (I) is dissolved in its free form in a solvent, e.g. an alcohol or water, an adequate amount of hydrochlorid acid or sodium hydroxide is added to the solution, the mixture is agitated at room temperature for an adequate period, then the solvent is distilled off, the residue is recrystallized and the salt of the compound of formula (I) is obtained. Suitable examples for such pharmaceutically acceptable salts additionally to the salt of hydrochloric acid are the salts of sulfuric acid, nitric acid, phosphoric acid, sulfonic acid, benzoic acid, succinic acid, tartaric acid and citric acid. Examples for pharmaceutically acceptable addition salts of bases additionally to the sodium salt are the potassium salt, the calcium salt and the magnesium salt.

The salts of compounds of formula (I) may be converted in usual manner into the free form of compounds. E.g. the salt of compound of formula (I) is dissolved in water, then an adequate amount of hydrochloric acid or sodium hydroxide is added to the solution, the mixture is agitated at room temperature for an adequate period, water is removed, the residue is distilled under reduced pressure or recrystallized from a solvent and the desired compound is obtained.

Acid or base addition salts of the compounds of the invention have the same inhibitory effect on thromboxane synthetase such as the corresponding compounds having a free amino radical or an acid radical.

The compounds of formula (II) may be prepared e.g. starting from the thiophen-2-carboxylic acids of formula (IV) known from the literature in accordance with the following synthesis scheme:

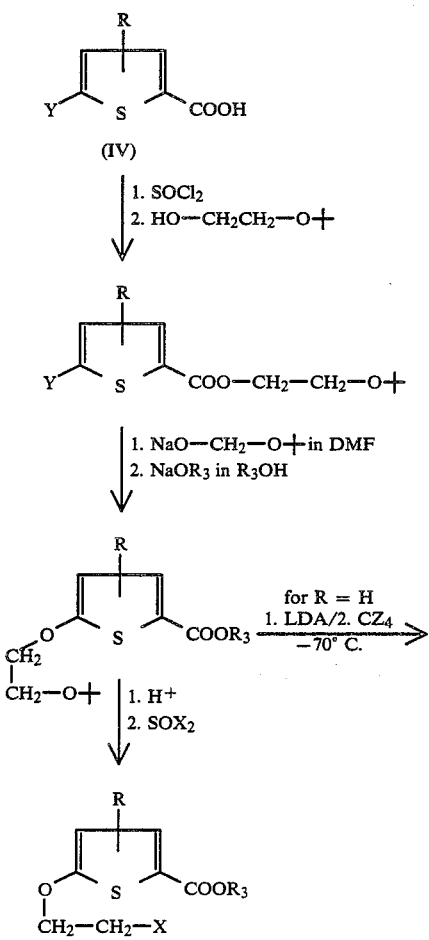

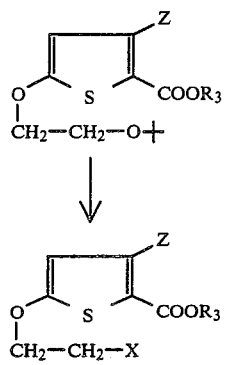

in which R=H or $CH_3$, $R_3$=$C_1$-$C_4$-alkyl, X=Cl or Br, Y=Cl, Br or I, Z=Cl or Br.

the following examples illustrate the invention without limiting it thereto.

EXAMPLE 1

5-[2-(1-Imidazolyl)-1-ethoxy]-thiophene-2-carboxylic acid methyl ester (formula I: R=H, $R_1$=$CH_3$)

1,58 g (33 mmol) of a 50% NaH-suspension in ligroin were washed three times with absolute benzene on a glass suction filter so as to remove the ligroin and introduced in not completely dry state into 20 ml of absolute DMF. To this suspension 2,25 g (33 mmol, MW 68,1) of imidazole dissolved in 10 ml of absolute DMF were dropped. Then it was stirred at 90° C. until the formation of $H_2$ had ceased, which required about 1 hour. It was cooled to room temperature and a solution of 6,6 g (30 mmol) of 5-(2-chloroethoxy)-thiophene-2-carboxylic acid methyl ester (formula II: $R_2$=H, $R_3$=$CH_3$, X=Cl) and 0,22 g (1,5 mmol) of NaI in 10 ml of absolute DMF were allowed to flow in. It was heated 1 hour to 70° C. After cooling the DMF was evaporated, the residue was partitioned between ether and 2N HCl, the aqueous phase was neutralized with solid $NaHCO_3$ and extracted with $CH_2Cl_2$. The $CH_2Cl_2$-phase was dried over $Na_2SO_4$ and evaporated in vacuo. Yield 4,0 g (53%). Melting point 93°–95° C. (benzene), colorless crystals.

In analogous way there were obtained:

5-[2-(1-Imidazolyl)-1-ethoxy]-3-methyl-thiophene-2-carboxylic acid methyl ester (formula I: R=3-$CH_3$, $R_1$=$CH_3$) melting point (ether) 79°–82° C. (50%).

5-[2-(1-Imidazolyl)-1-ethoxy]-4-methyl-thiophene-2-carboxylic acid methyl ester (formula I: R=4-methyl, $R_1$=$CH_3$) melting point (toluene) 102°–105° C. (44%).

The starting material may be prepared as follows:

2-Chloro-3-methylthiophene 50 g (0,51 mol) of 3-methylthiophene were heated to boiling and 71,43 g (0,53 mol) of $SO_2Cl_2$ were dropped thereto during ½ hour. Then it was refluxed further 1½ hours and the reaction solution was fractionated distilled over a packed column. Yield 35,3 g (52%), b.p. 152°–155° C./1013 mbar, $n_D^{20}$=1,5408.

3-Bromo-3-methylthiophene 196,23 g (2 mol) of 3-methylthiophene were dissolved in 600 ml of $CCl_4$, the solution was cooled to −10° C. and 319,64 g (2 mol) of $Br_2$ dissolved in 400 ml of $CCl_4$ were added at this temperature during 2 hours thereto. Then it was allowed to warm up to room temperature, stirred for 2 hours and the reaction solution was fractionated distilled at 22 mbar. Yield 199 g(56%), b.p. 66° C./22 mbar, $n_D^{20} = 1,5729$.

2-Bromo-5-chloro-3-methylthiophene

To 50 g (0,28 mol) of 2-bromo-3-methylthiophene 30,7 g (0,294 mol) of $SO_2Cl_2$ were added with stirring such that the temperature did not exceed 10° C. It was stirred 2 hours at room temperature and the reaction solution was fractionated distilled at 22 mbar. Yield 37 g (62%), b.p. 90°–114° C./22 mbar.

5-Chloro-3-methylthiophene 448,53 g of Zn-dust were suspended in 722 ml of $H_2O$, 280 g of acetic acid were added, the reaction mixture was refluxed and 361,11 g of 2-bromo-5-chloro-3-methylthiophene were dropped thereto. After 15 h reflux it was distilled off over a distillation bridge, the organic phase of the distillate was separated, washed with saturated $NaHCO_3$-solution and fractionated distilled at normal pressure. Yield 133 g (59%), b.p. 153°–167° C./1013 mbar, $n_D^{20} = 1,5365$.

(5-Chloro-4-methyl-2-thienyl)-methylketone

A mixture of 20 g (0,15 mol) of 2-chloro-3-methylthiophene and 18,6 g (0,18 mol) of acetic acid anhydride were heated to 70° C. and 1,8 ml of orthophosphoric acid were dropped thereto such that the reaction temperature remained below 75° C. Then it was stirred 3 hours at 100° C., 50 ml of $H_2O$ were added, the organic phase was extracted twice with 10 ml of saturated $NaHCO_3$-solution, dried over $Na_2SO_4$ and fractionated distilled in vacuo. Yield 15,8 g (60%), b.p. 85°–88° C./4 mbar.

In analogous way, however, with a maximum of reaction temperature of 25° C., there is obtained:

(5-Chloro-3-methyl-2-thienyl)-methylketone, b.p. 104°–110° C./ 7 mbar, $n_D^{20} = 1,5771$ (64%).

5-Chloro-4-methyl-thiophene-2-carboxylic acid 160 g of ice were added to a solution of 43,21 g (1,08 mol) of NaOH in 80 ml of water and 28,5 g (0,40 mol) of $Cl_2$ were introduced such that the temperature did not exceed 5° C. Then this NaOCl-solution was heated to 55° C. and 14,9 g (85,3 mmol) of (5-chloro-4-methyl-2-thienyl)-methylketone were added at once under stirring. The reaction mixture was heated to 60° C. for 1 hour under stirring, cooled to room temperature, 15 g of $NaHSO_3$ were added, extracted by shaking with $CH_2Cl_2$ and acidified with conc. HCl. The colorless crystals were sucked off, washed with water and dried in vacuo at 80° C. Yield 11,45 g (76%), melting point ($CH_3/H_2O$) 175°–178° C.

In analogous way there is obtained:

5-Chloro-3-methyl-thiophene-2-carboxylic acid, melting point (methanol/$H_2O$) 149°–152° C. (90%).

Chloride of 5-chlorothiophene-2-carboxylic acid 44,3 g (0,37 mol) of $SOCl_2$ were added to 40,0 g (0,256 mol) of 5-chlorothiophene-2-carboxylic acid, refluxed for 4 hours, the excess of $SOCl_2$ was evaporated and the residue was used in crude state in the next step. Yield 46,1 g (99%), b.p. 103°–105° C./14 mbar, colorless oil.

In analogous way there were obtained:

Chloride of 5-chloro-4-methyl-thiophene-2-carboxylic acid and Chloride of 5-chloro-3-methyl-thiophene-2-carboxylic acid, both were used in crude state in the next step.

[2-(2-Methyl-2-propoxy)-1-ethyl]-ester of 5-chlorothiophene-2-carboxylic acid 36,2 g (0,2 mol) of 5-chlorothiophene-2-carboxylic acid chloride were dropped rapidly under stirring to a mixture consisting of 26,0 g (0,22 mol) of 2-tert.-butoxyethanol, 22,22 g (0,22 mol) of triethylamine in 100 ml of absolute THF at room temperature. Then it was stirred for 1 hour at room temperature and for 10 minutes at boiling temperature. After cooling it was evaporated in vacuo, the residue was partitioned between ether and $NaHCO_3$-solution, the organic phase was dried und evaporated in vacuo and then distilled in vacuo. Yield of crude material 50,3 g (96%), yield 42,3 g (80%) of a colorless oil, b.p. 90°–93° C./0,007 mbar.

In analogous way there were obtained:

[2-(2-Methyl-2-propoxy)-1-ethyl]-ester of 5-chloro-4-methylthiophene-2-carboxylic acid, b.p. 136° C./0,7 mbar (84%), and

[2-(2-Methyl-2-propoxy)-1-ethyl]-ester of 5-chloro-3-methylthiophene-2-carboxylic acid, b.p. 137°–139° C./10 mbar (72%).

[2-(2-Methyl-2-propoxy)-1-ethyl]-ester of 5-[2-(2-Methyl-2-propoxy)-1-ethoxy]-thiophene-2-carboxylic acid 43,95 g (1,044 mol) of a 57% NaH-suspension in ligroin were washed three times with absolute benzene on a glass suction filter so as to remove the ligroin and added in not completely dry state in small portions to a mixture consisting of 123,5 g (1,044 mol) of 2-tert.-butoxyethanol and 300 ml of fresh distilled absolute DMF under stirring. The reaction temperature was kept below 45° C. After completion of the addition 180 g (0,069 mol) of the [2-(2-methyl-2-propoxy)-1-ethyl]-ester of 5-chlorothiophene-2-carboxyclic acid were dropped thereto with stirring and then kept at 65° C. for 1 hour. It was cooled to room temperature, 19,8 g (0,33 mol) of glacial acetic acid were added, partitioned between ether and sodium hydrogen carbonate solution, the organic phase was dried (sodium sulfate) and evaporated in vacuo. The oily residue had a weight of 209 g (65%) and was used in the next step without further purification, b.p. 135°–138° C./0,014 mbar, colorless oil.

In analogous way there were obtained:

[2-(2-Methyl-2-propoxy)-1-ethyl]-ester of 3-methyl-5-[2-(2-methyl-2-propoxy)-1-ethoxy]-thiophene-2-carboxylic acid, melting point (ether/petroleum ether) 43°–46° C., and

[2-(2-Methyl-2-propoxy)-1-ethyl]-ester of 4-methyl-5-[2-(2-methyl-2-propoxy)-1-ethoxy]-thiophene-2-carboxylic acid, oil. Both compounds were used as crude products in the next step.

5-[2-(Methyl-2-propoxy)-1-ethoxy]-thiophene-2-carboxylic acid methyl ester 204 g of crude [2-(2-methyl-2-propoxy)-1-ethyl]-ester of 5-[2-(2-methyl-2-propoxy)-1-ethoxy]-thiophene-2-carboxylic acid were refluxed together with 11,84 g of $NaOCH_3$ in 500 ml of absolute methanol for 11 hours. After cooling 13,5 g of glacial acetic acid were added and the methanol was evaporated at 30° C. The residue was partitioned between methylene chloride and sodium hydrogen carbonate solution, the organic phase was dried, evaporated and distilled in vacuo. Yield 105 g (93%), b.p. 139°–145° C./0,14 mbar, melting point 41°–42° C. (petroleum ether), colorless crystals.

In analogous way there were obtained:

3-Methyl-5-[2-(2-methyl-2-propoxy)-1-ethoxy]-thiophene-2-carboxylic acid methyl ester, b.p. 136°–150° C./1,4 mbar (45%), and 4-Methyl-5-[2-(2-methyl-2-propoxy)-1-ethoxy]-thiophene-2-carboxylic acid methyl ester, b.p. 155°–160° C./1 mbar (33%).

5-(2-Hydroxy-1-ethoxy)-thiophene-2-carboxylic acid methyl ester 100 ml of conc. hydrochloric acid were added to 105 g (0,41 mol) of 5-[2-(2-methyl-2-propoxy)-1-ethoxy]-thiophene-2-carboxylic acid and shaken for 15 minutes. Then 100 ml of water were added and it was extracted several times with methylene chloride. The organic phases were combined, shaken with sodium hydrogen carbonate solution, dried and evaporated. Yield 76 g (92%). The product could be used in the next step without further purification, b.p. 104°–107° C./0,014 mbar, colorless oil.

In analogous way there were obtained:

3-Methyl-5-(2-hydroxy-1-ethoxy)-thiophene-2-carboxylic acid methyl ester, melting point (petroleum ether) 56°–61° C. (98%) and 4-Methyl-5-(2-hydroxy-1-ethoxy)-thiophene-2-carboxylic acid methyl ester, melting point (benzene) 70°–72° C. (90%).

5-(2-Chloro-1-ethoxy)-thiophene-2-carboxylic acid methyl ester

A mixture consisting of 45,5 g (0,225 mol) of 5-(2-hydroxy-1-ethoxy)-thiophene-2-carboxylic acid methyl ester and 17,80 g (0,225 mol) of pyridine in 20 ml of absolute chloroform were cooled with mechanical stirring to −40° C. and 29,45 g (0,248 mol) of $SOCl_2$ were added such that the reaction temperature did not exceed −35° C. After completion of the addition the cooling bath was removed and the reaction mixture was allowed to warm up. Then it was heated to 60° C. for 1 hour, cooled, partitioned between ether and water, the organic phase was shaken mit 2N HCl and then with a $NaHCO_3$-solution, dried and evaporated in vacuo. Yield 45,14 g (91%), melting point 54°–55° C. (petroleum ether), colorless crystals.

In analogous way there were obtained:

3-Methyl-5-(2-chloro-1-ethoxy)-thiophene-2-carboxylic acid methyl ester, melting point ($MeOH/H_2O$) 47°–50° C. (86%), and 4-Methyl-5-(2-chloro-1-ethoxy)-thiophene-2-carboxylic acid methyl ester, melting point (petroleum ether) 75° C. (90%).

EXAMPLE 2

4-Chloro-5-[2-(1-imidazolyl)-1-ethoxy]-thiophene-2-carboxylic acid methyl ester (formula I: R=4-Cl, $R_1$=CH₃)

0,15 g of 5-[2-(1-imidazolyl)-1-ethoxy]-thiophene-2-carboxylic-acid methyl ester (formula I: R=H, $R_1$=CH₃) were dissolved in 5 ml of absolute chloroform, cooled to −40° C. and 0,16 g (1,19 mol) of $SO_2Cl_2$ were dropped thereto such that the temperature did not exceed −35° C. After standing over night it was evaporated in vacuo, the residue was partioned between 2N HCl and ether, the aqueous phase was extracted several times with ether, neutralized with sodium hydrogen carbonate and extracted several times with methylene chloride. The combined methylene chloride phases were dried (sodium sulfate) and evaporated, the residue from the evaporation was separated by column chromatography (eluant: benzene/ethanol 9:1). Yield 73 mg (43%), melting point 97°–99° C. (benzene/ether), colorless crystals.

EXAMPLE 3

5-[2-(1-Imidazolyl)-1-ethoxy]thiophene-2-carboxylic acid hydrochloride (formula I: R=H, $R_1$=H) (LG82-4-00) 2,52 g (10 mmol) of 5-[2-(1-Imidazolyl)-1-ethoxy]-thiophene-2-carboxylic acid methyl ester (formula I: R=H, $R_1$=CH₃) were stirred with 0,48 g (12 mmol) of NaOH in 50 ml of water at room temperature, until the suspension became clear (about 3 hours). Then the reaction mixture was concentrated in vacuo, acidified with 10 ml of 2N hydrochloric acid, evaporated in vacuo, the residue was evaporated twice with benzene (20 ml) so as to remove residual moisture, boiled with 50 ml of absolute ethanol, filtered off from sodium chloride and the ethanolic solution was evaporated. The crystalline residue was dissolved by heating in 100 ml of absolute ethanol, cooled and the product was precipitated by addition of ether. Yield 2,18 g (80%), melting point 164°–166° C., colorless crystals.

In analogous way there were obtained:

4-Chloro-5-[2-(1-imidazolyl)-1-ethoxy]-thiophene-2-carboxylic acid hydrochloride (formula I: R=4-Cl, $R_1$=H), melting point (ethanol) 220° C. (decomp.), colorless crystals (LG82-4-01).

3-Methyl-5-[2-(1-imidazolyl)-1-ethoxy]-thiophene-2-carboxylic acid hydrochloride (formula I: R=3-$CH_3$, $R_1$=H) (saponification temperature 65° C.), melting point (ethanol/ether 199°–202° C.

4-Methyl-5-[2-(1-imidazolyl)-1-ethoxy]-thiophene-2-carboxylic acid hydrochloride (formula I: R=4-$CH_3$, $R_1$=H), melting point (ethanol/ether) 187°–190° C.

An in vitro-study of two compounds of the inventions, namely LG 82-4-00 and LG 82-4-01, for the inhibition of thromboxane (TX) formation on platelet aggregation showed that the compounds of the invention are specific inhibitors of thromboxane synthetase.

In 0,6 IU/ml thrombin stimulated human washed platelets the $IC_{50}$ ($\mu M$) for inhibition of TX formation (measured by $TXB_2$ specific radioimmunoassay) was 1,1 for LG 82-4-00 and 1,3 for LG 82-4-01. The two substances inhibited $TXB_2$-formation and 1–2 $\mu g/ml$ collagen induced platelet aggregation by more than 95%.

Neither LG 82-4-00 nor LG 82-4-01 had vasoconstrictor, proaggregatory or antagonistic activity or affected primary wave ADP aggregation (P >0,05).

At 10 $\mu m$ there was no inhibition of arachidonic acid-induced $PGI_2$ formation from bovine coronary artery slices.

The compounds of the invention can be used in form of tablets or capsules containing a dose unit of the compounds together with diluents such as corn starch, calcium carbonate, dicalcium phosphate, alginic acid, lactose, magnesium stearate, Primogel (trade mark) or talcum for oral application. Tablets are prepared in conventional manner by granulating and compressing the ingredients, capsules are prepared by filling the ingredients into hard gelatine capsules of suitable size.

The compounds of the invention can be administered also parenterally, e.g. by intramuscular, intravenous or subcutaneous injection. For parenteral application it is most convenient to use the compounds in form of a sterile aqueous solution which may contain other dissolved substances such as tonic substances and substances for adjusting the pH-value. The compounds can be added to distilled water and the pH-value can be adjusted by using an acid such as citric acid, lactic acid or hydrochloric acid to 3 to 6. Sufficient solutes such as dextrose or saline solution may be added so as to make the solution isotonic. The obtained solution can be sterilized and filled into sterile glass ampoules of suitable size, so that they contain the desired volume of the solution. The compounds of the invention may be administered also by infusion of a parenteral formulation as described above into a vein.

For oral administration to human beings it is supposed that the daily dosage of a compound of the invention is in the range of from 0,1 to 20 mg/kg per day for a typical adult person weighing 70 kg. For the parenteral administration it is supposed that the daily dosage of a compound of formula (I) will be 0,01 to 0,5 mg/kg per day for a typical adult person. Therefore, tablets or capsules may contain usually 5 to 150 mg of the active compound for the oral application up to three times per day. The dosage units for the parenteral application may contain 0,5 to 35 mg of the active compound. Therefore, a typical ampoule could be a 10 ml-ampoule containing 5 mg of the active compound in 6 to 10 ml solution.

However, in each case the physician will determine the real dosage most suitable for the patient, which dosage may vary in accordance with the age, the weight and the reaction of the patient.

What is claimed is:

1. A derivative of the thiophene-2-carboxylic acid of the general formula

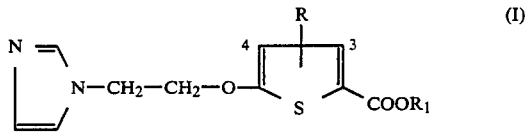

in which R in position 3 or 4 of the thiophene nucles is hydrogen, methyl, chlorine or bromine and $R_1$ is hydrogen or $C_1$-$C_4$-alkyl, and its pharmaceutically acceptable acid or base addition salts.

2. 5-[2-(1-Imidazolyl)-1-ethoxy]-thiophene-2-carboxylic acid methyl ester according to claim 1.

3. 5-[2-(1-Imidazolyl)-1-ethoxy]-3-methyl-thiophene-2-carboxylic acid methyl ester according to claim 1.

4. 5-[2-(1-Imidazolyl)-1-ethoxy]-4-methyl-thiophene-2-carboxylic acid methyl ester according to claim 1.

5. 4-Chloro-5-[2-(1-imidazolyl)-1-ethoxy]-thiophene-2-carboxylic acid methyl ester according to claim 1.

6. 5-[2-(1-Imidazolyl)-1-ethoxy]-thiophene-2-carboxylic acid hydrochloride according to claim 1.

7. 4-Chloro-5-[2-(1-imidazolyl)-1-ethoxy]-thiophene-2-carboxylic acid hydrochloride according to claim 1.

8. 3-Methyl-5-[2-(1-imidazolyl)-1-ethoxy]-thiophene-2-carboxylic acid hydrochloride according to claim 1.

9. 4-Methyl-5-[2-(1-imidazolyl)-1-ethoxy]-thiophene-2-carboxylic acid hydrochloride according to claim 1.

10. A pharmaceutical active composition comprising a therapeutically effective amount of a compound of claim 1, 2, 3, 4, 5, 6, 7, 8 or 9 effective for treating a disease caused by thromboxane $A_2$ together with a pharmaceutically acceptable carrier or diluent.

* * * * *